United States Patent
Falahee

(10) Patent No.: US 8,262,696 B2
(45) Date of Patent: Sep. 11, 2012

(54) MULTILEVEL FACET/LAMINAR FIXATION SYSTEM

(75) Inventor: Mark H. Falahee, Ann Arbor, MI (US)

(73) Assignee: Medical Design, LLC, Ann Arbor, MI (US)

(*) Notice: Subject to any disclaimer, the term of this patent is extended or adjusted under 35 U.S.C. 154(b) by 857 days.

(21) Appl. No.: 11/678,892

(22) Filed: Feb. 26, 2007

(65) Prior Publication Data

US 2007/0233093 A1 Oct. 4, 2007

Related U.S. Application Data

(60) Provisional application No. 60/776,450, filed on Feb. 24, 2006.

(51) Int. Cl.
*A61B 17/70* (2006.01)
(52) U.S. Cl. ......................... 606/247; 606/246
(58) Field of Classification Search .......... 606/246–279, 606/300–321, 60, 61, 70–73
See application file for complete search history.

(56) References Cited

U.S. PATENT DOCUMENTS

| | | | |
|---|---|---|---|
| 7,008,423 B2* | 3/2006 | Assaker et al. | 606/250 |
| 7,658,753 B2* | 2/2010 | Carl et al. | 606/257 |
| 2003/0040746 A1* | 2/2003 | Mitchell et al. | 606/61 |
| 2004/0127906 A1* | 7/2004 | Culbert et al. | 606/72 |
| 2005/0049705 A1* | 3/2005 | Hale et al. | 623/17.11 |
| 2005/0131537 A1* | 6/2005 | Hoy et al. | 623/17.11 |
| 2006/0058790 A1* | 3/2006 | Carl et al. | 606/61 |

* cited by examiner

*Primary Examiner* — Eduardo C Robert
*Assistant Examiner* — Christina Negrelli
(74) *Attorney, Agent, or Firm* — Gifford, Krass, Sprinkle, Anderson & Citkowski, P.C.

(57) ABSTRACT

In a spinal stabilization system a facet fixation device is interconnected to an anchor or fixation device driven into a portion of the spine. The facet fixation device has a proximal head and a distal fastener providing compression across a facet joint. A rigid or elastic member interconnects the proximal head of the facet fixation device to the anchor or fixation device, facilitating static or dynamic stabilization. The facet fixation device may extend directly across the facet joint, or a translaminar or laminar transverse process facet (LTPF) fixation device may be used. In the preferred embodiment the facet fixation device includes a distal tip which is self-cutting and tapping. The anchor may be a pedicle screw. The fixation device itself be a facet fixation device, and the facet fixation device may be connected to the anchor or fixation through two members joined with a coupling unit.

4 Claims, 4 Drawing Sheets

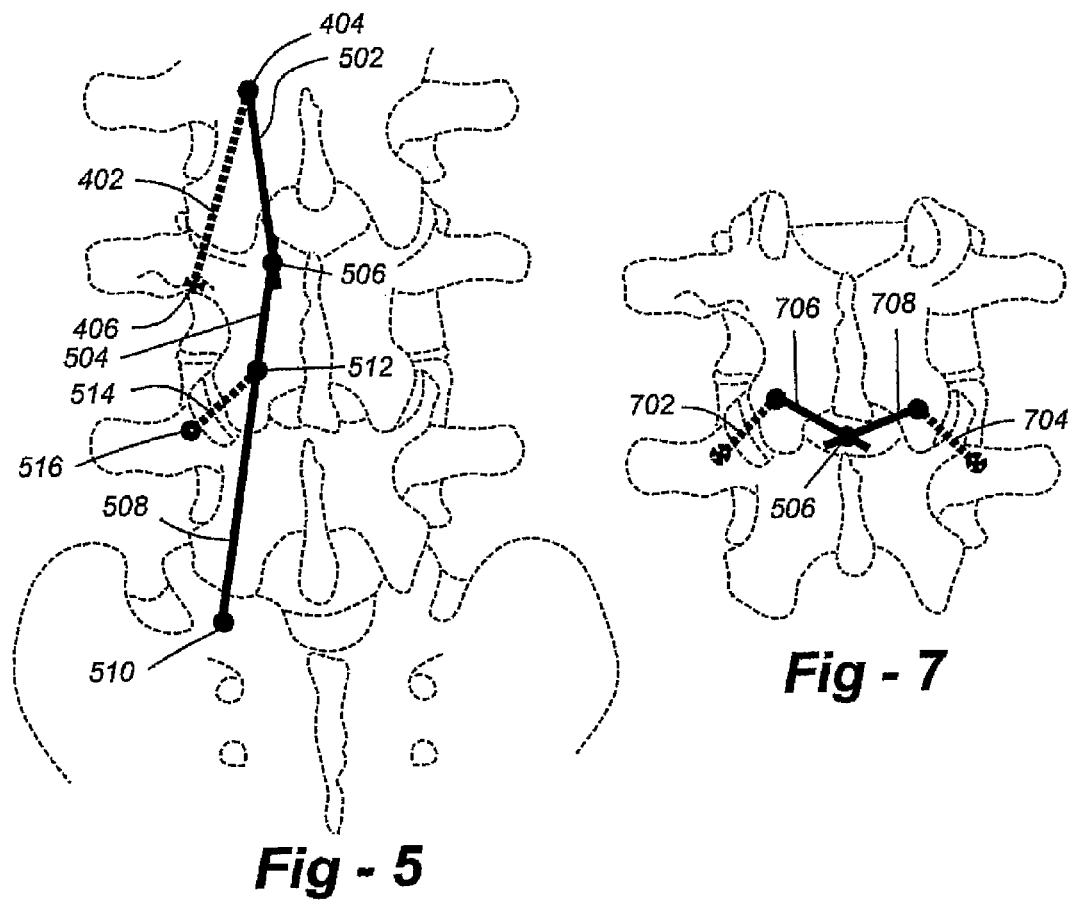
Fig - 5
Fig - 7
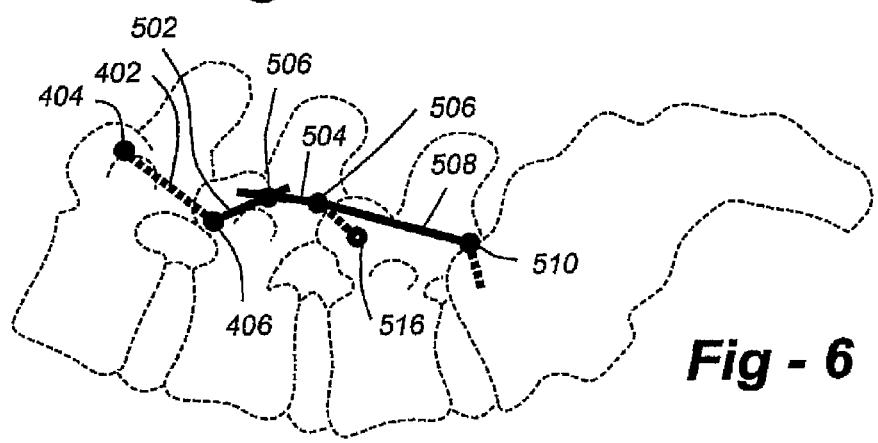
Fig - 6

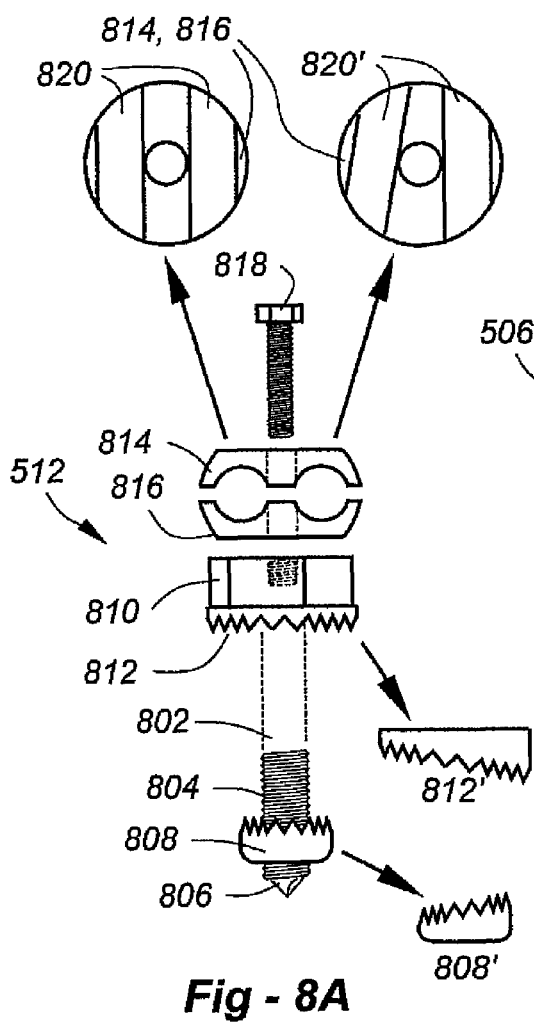
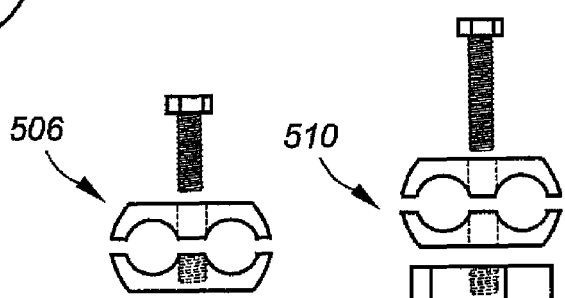
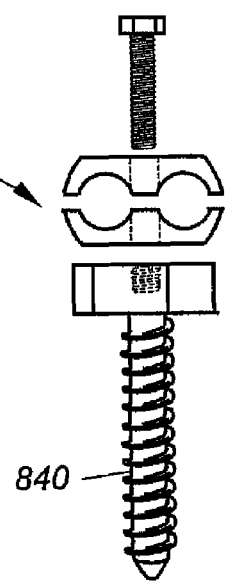
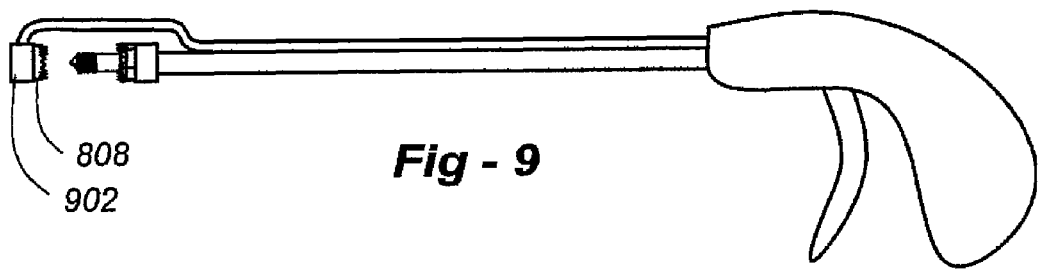

MULTILEVEL FACET/LAMINAR FIXATION SYSTEM

REFERENCE TO RELATED APPLICATION

This application claims priority from U.S. Provisional Patent Application Ser. No. 60/776,450, filed on Feb. 24, 2006, the entire content of which is incorporated herein by reference.

FIELD OF THE INVENTION

This invention relates generally to spinal fixation and, in particular, to multilevel facet/laminar fixation apparatus and methods.

BACKGROUND OF THE INVENTION

Current posterior spine implantation instrumentation devices utilize pedicle fixation to secure rods or plates to the posterior spine. Reference is made to FIG. 1, which shows the stabilization of two spinal levels, with the understanding that certain conditions, such as scoliosis, require immobilization and alignment of multiple levels. In the figure, the upper vertebral body is indicated at 102, with the lower vertebral body being indicated at 103. The disc between the bodies is shown as 108. The upper vertebral body 102 includes transverse processes 106, and spinous process 112. The superior articular processes 104 are shown with respect to the upper vertebral body, in the absence of an entire facet joint, though a completed joint is shown at 110 between the upper and lower bodies.

A typical prior-art plate/rod fixation system includes longitudinal members 120, 122 which are anchored via pedicle screws 124, 126. Often link members, such as 128, are utilized to offset the members 120, 122 into an appropriate region of the spine, on either side of the spinous processes. Rods having a circular cross-section are ordinarily used, though in this application, other geometries, including rectangular "plates" are common as well.

Various existing fixation systems utilize the facet joint as opposed to pedicle screw and rod/plate alignment. FIG. 2, for example, shows an existing translaminar fixation system, which utilizes some sort of a fastener 202, typically having a drive head 204. The fastener is oriented through the lamina on one side of the vertebral body, and down through the facet joint on the other side of the spinal column. The fastener, indicated at 202, is typically a threaded screw which is inserted following guide wire and pilot hole formation.

Also in the prior-art, is the use of facet fixation directly across a facet joint, as indicated in FIG. 3. Here, a fastener having a threaded portion 302 is driven through the joint, as shown, utilizing some sort of a proximal drive head 304. Approaches utilizing transfacet fixation are presently stand-alone devices, and are not linked together, or to pedicle screws via any rod/plate system.

SUMMARY OF THE INVENTION

This invention resides in a spinal stabilization system wherein a facet fixation device is interconnected to an anchor or fixation device driven into a portion of the spine. In the preferred embodiments the facet fixation device has a proximal head and a distal fastener providing compression across a facet joint. A rigid or elastic member interconnects the proximal head of the facet fixation device to the anchor or fixation device, facilitating static or dynamic stabilization.

The facet fixation device may extend directly across the facet joint, or a translaminar or laminar transverse process facet (LTPF) fixation device may be used. In the preferred embodiment the facet fixation device includes a distal tip which is self-cutting and tapping. The anchor may be a pedicle screw. The fixation device itself be a facet fixation device, and the facet fixation device may be connected to the anchor or fixation through two members joined with a coupling unit.

BRIEF DESCRIPTION OF THE DRAWINGS

FIG. 5 is a posterior view of the more comprehensive embodiment of the invention, utilizing a laminar transverse process approach, a locking facet fixation component, and a pedicle screw that engages with the sacrum;

FIG. 6 is a lateral view of the system of FIG. 5;

FIG. 7 is a posterior view of another embodiment of the invention, wherein a universal joint connector is used to stabilize bilateral transfacet fixation devices;

FIG. 8A is an exploded view of a locking mechanism utilized for laminar transverse process fixation; translaminar fixation; or locking facet fixation;

FIG. 8B is a drawing of a preferred universal joint connector;

FIG. 8C is a drawing that shows a pedicle screw fixation apparatus according to the invention;

FIG. 9 is a drawing that shows a facet gun that may be used for direct facet fixation or, alternatively, translaminar, fractured bone, corrective osteotomy and other stabilization applications;

DETAILED DESCRIPTION OF THE PREFERRED EMBODIMENTS

Figure 1:
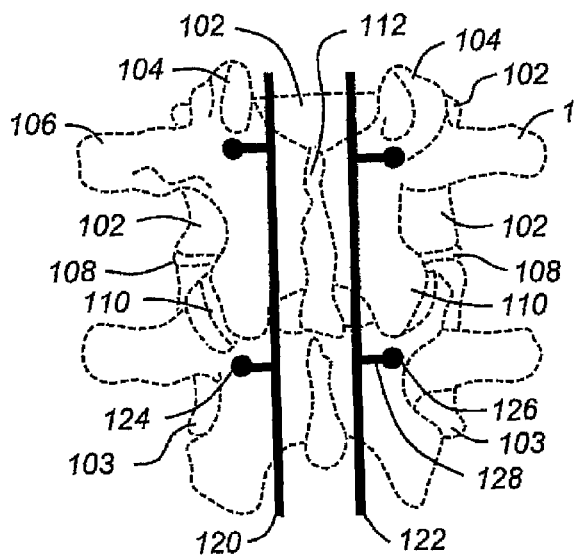
FIG. 1 is a posterior view of an existing, typical rod/plate spinal alignment system anchored with pedicle screws.
Figure 2:
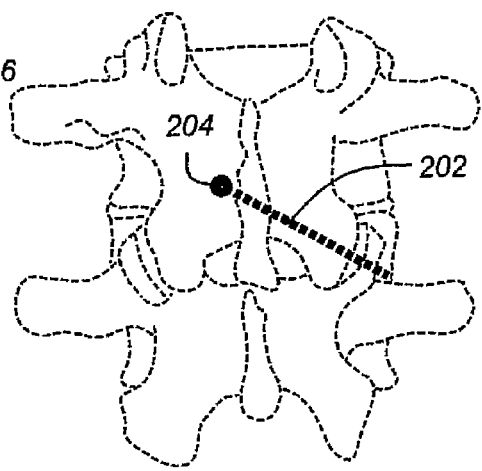
FIG. 2 is a posterior view of an existing translaminar, transfacet alignment system utilizing a screw that courses through the lamina and through the facet joint on the other side.
Figure 3:
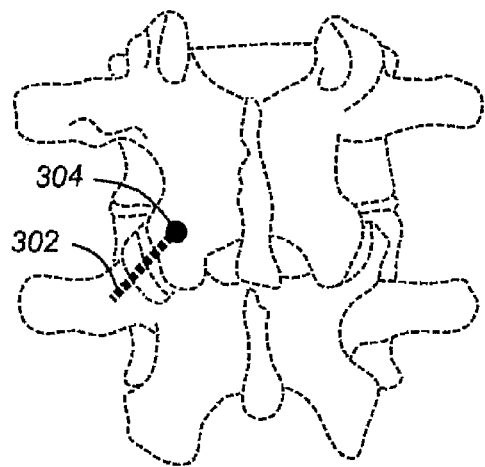
FIG. 3 is a drawing of a typical existing transfacet screw fixation system.
Figure 4:
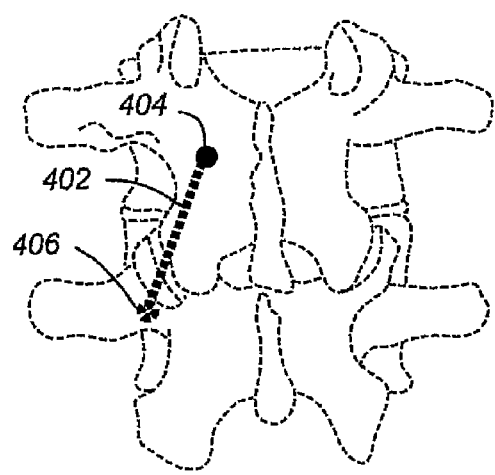
FIG. 4 is a drawing of a laminar transverse process fixation (TPF) fixation approach according to the invention, wherein the distal end of the fastener includes a component that facilitates compression across the facet joint.

Having discussed the prior art, the reader's attention is now directed to FIG. 4, which illustrates a laminar transverse process fixation (LTPF) technique according to the invention. In contrast to existing techniques, including transfacet fixation techniques, the invention prescribes the use of a fixation component having a shaft 402, with a proximal head/driver 404, and a distal fastener 406, facilitating compressive fixation across the facet joint, and other applications disclosed herein.

Referring to FIG. 5, the laminar transverse process fixation technique is carried out in conjunction with a facet fixation component 514, having proximal drive portion 512, and a distal fastener 516 facilitating compressive fixation. A rod or plate 504 in this instance is used to connect to the head of the LTPF system through a rod or plate 502, the elements 502, 504, being interconnected with a universal joint connector 506 discussed in further detail below. From the head 512 of the transfacet fixator, there extends a rod 508 to a pedicle screw system 510, also described in further detail below. Note that the element 504 and 508 may be independent or separate, depending on the overall orientation of the system. FIG. 6 is a side-view of the drawing of the system of FIG. 5, showing the relationship among the various components.

Both FIGS. 5 and 6 show a comprehensive embodiment involving the interconnection between LTPF, locking facet fixation (LFF), and pedicle-screw (PS) fixation, the invention broadly involves the interconnection of any system used to stabilize a facet joint, whether through direct transfacet, translaminar or LTPF fixation, then utilizing a rod or plate system, to interconnect that system to any other. For example, as shown in FIG. 7, two transfacet fixation systems 702, 704, may be linked together through member 706, 708, again, through universal joint connector 506. Note that in this drawing and others, bony material that must be removed in order to facilitate the procedure is not necessarily shown. For example, in some instances, one or more transverse processes, spinous process(es), and the like, may need to be resected in order to facilitate access.

FIG. 8A is a drawing which illustrates a typical compression fixator according to the invention, such as the LTPF system of FIG. 4 or the facet fixation system 512 shown in FIG. 5. The apparatus includes a proximal portion, preferably including a tooth engaging surface 812, coupled to a drive portion 810, which may be hexagonal, or any other shape enabling torque to be applied. The proximal assembly attaches to a shaft 802, which includes distal threads 804 that engage with a proximal 808. In the preferred embodiment, the distal tip includes a portion 806 that facilitates self-cutting, tapping, and locking, as described in further detail herein. As shown at 812', 808', the surfaces of the engagement members 812, 808, may be angled to facilitate conforming with different surfaces, which may not be parallel to one another.

Attached to the drive component 810, is a rod/plate engagement unit including upper and lower halves 814, 816, which are compressed and locked into drive component 810 through fastener 818. As shown in the upper portion of the drawing, the channels 820 in the members 814, 816 may be parallel, or, alternatively, as shown at 820' they may be angled relative to one another, depending upon the case. Typically, the surgeon will be provided with multiple portions 814, 816, to adjust for the angle of the plates or rods being dressed and locked therethrough. Although a polyaxial fixation system may be used, many of which are known or available to those of skill in the art, the system shown in FIG. 8A is preferred for its relatively low profile.

FIG. 8B is a drawing which shows a typical universal joint connector at 506, including upper and lower components that may have parallel or nonparallel guides to receive plates or rods. FIG. 8C is a drawing which shows a typical pedicle screw fixation system of the type indicated at 510, including a pedicle screw portion 840. Although the embodiments shown includes rods (or plates) having a uniform cross-section, other embodiments, wherein the distal or proximal ends of the rods or plates are enlarged to facilitate locking or accommodating as well.

In the embodiments of FIG. 8A and FIG. 8C, the fastener or pedicle screw portions would be driven in first, using the drive head, such 810, after which the plate/rod fixation system would be attached, utilizing fasteners such as 818. Although a geometric-head type fastener is shown, it will be appreciated that hex head and other types of fastener arrangements are equally accommodated.

Although the invention is not limited to fasteners of the type including a distal component for compressive fixation, compression with a distal fastener is preferred for stability. Such devices may be delivered by the facet gun mechanism illustrated in FIG. 9, which includes, among other features, a distal holder 902, which facilitates the temporary positioning of distal component 808 shown in FIG. 8A.

Figure 10:
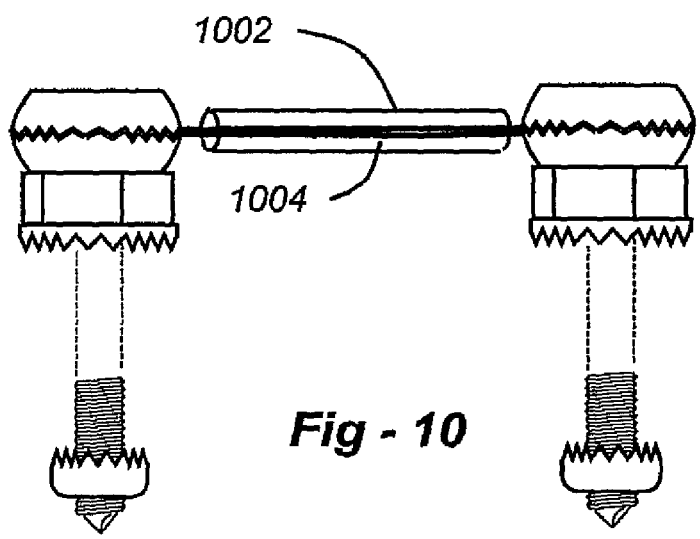
FIG. 10 is a drawing which shows the way in which the instant invention may be used for dynamic stabilization.
Figure 11:
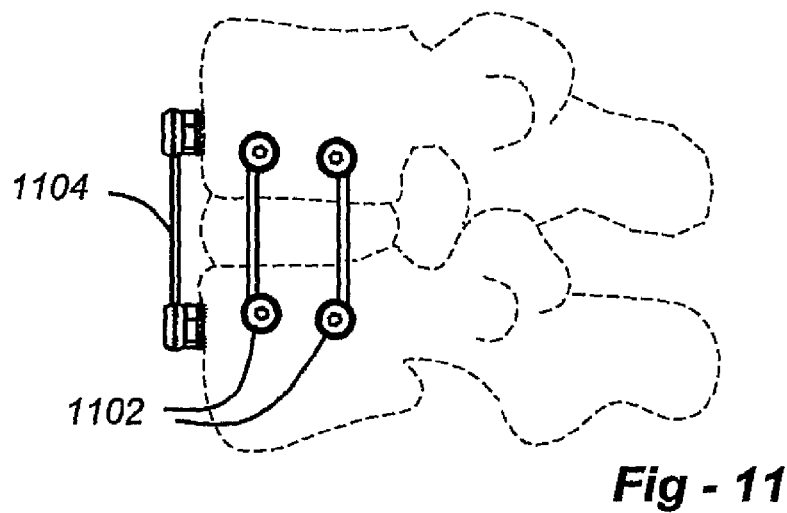
FIG. 11 is a drawing that shows the way in which the invention may be used for anterior/lateral vertebral segmental fixation.

Nor is the invention limited strictly to entirely rigid systems, in that flexible or partially pliable/resilient members may be used for dynamic stabilization purposes. For example, as shown in FIG. 10, an elastic cord 104 may be used to provide some extension motion, whereas this elastic sleeve 1002 may be provided with the cord 1004, or separately, to eliminate flexion or other degrees of freedom. The invention is also applicable to anterior and/or lateral vertebral segmented fixation, wherein one or more connectors 1104 may be used anteriorally, with one or more fasteners 1102 being used laterally.

Figure 12:
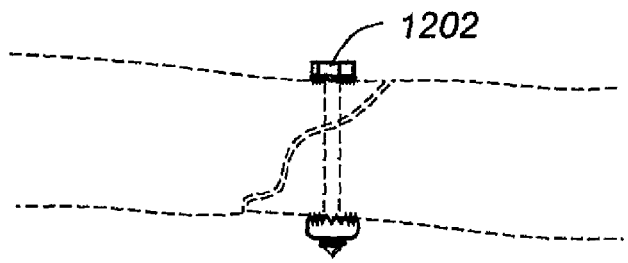
FIG. 12 is a side-view drawing that shows the way in which the invention may be applied to locking both fractured bone fixation.
Figure 13:
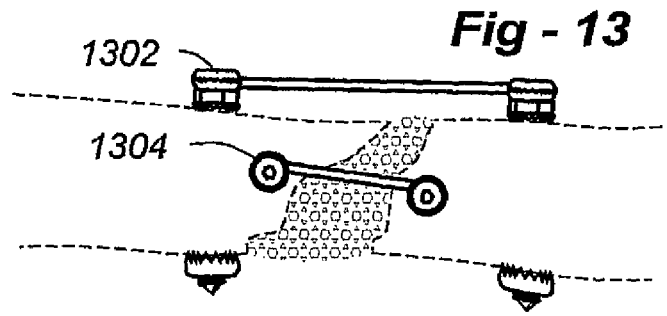
FIG. 13 is a drawing that shows the way in which the invention may be applied to corrective osteotomy and stabilization or alignment limb lengthening as part of a bony deformation correction approach.

FIG. 12 shows the way in which a fractured bone may be locked into position utilizing a compressive fastener 1202 according to the invention, and FIG. 13 illustrates the way in which a bony deformity may be corrected through alignment and limb lengthening, utilizing fasteners 1302 and/or 1304 to facilitate corrective osteotomy and stabilization.

I claim:

1. A spinal stabilization system, comprising:
   an anchor or fixation device driven into a portion of a spine;
   a facet fixation device having a proximal head, a threaded shaft, and a distal threaded fastener providing compression across a facet joint;
   a member interconnecting the proximal head of the facet fixation device to the anchor or fixation device; and
   wherein the member includes an elastic component facilitating at least a degree of dynamic stabilization.

2. A spinal stabilization system, comprising:
   an anchor or fixation device driven into a portion of a spine;
   a facet fixation device having a proximal head, a threaded shaft, and a distal threaded fastener providing compression across a facet joint;
   a member interconnecting the proximal head of the facet fixation device to the anchor or fixation device; and
   wherein the proximal head of the facet fixation device includes a bone-engaging surface with a plurality of bone-engaging teeth.

3. A spinal stabilization system, comprising:
   an anchor or fixation device driven into a portion of a spine;
   a facet fixation device having a proximal head, a threaded shaft, and a distal threaded fastener providing compression across a facet joint;
   a member interconnecting the proximal head of the facet fixation device to the anchor or fixation device; and
   wherein the distal threaded fastener of the facet fixation device includes a bone-engaging surface with a plurality of bone-engaging teeth.

4. A spinal stabilization system, comprising:
   an anchor or fixation device driven into a portion of a spine;

a facet fixation device having a proximal head, a threaded shaft, and a distal threaded fastener providing compression across a facet joint;

a member interconnecting the proximal head of the facet fixation device to the anchor or fixation device; and wherein the proximal head of the facet fixation device includes a bone-engaging surface which is angled relative to the shaft.

* * * * *